United States Patent [19]

Coates et al.

[11] 4,035,056

[45] July 12, 1977

[54] BIPHENYL DERIVATIVE COMPOUNDS AND LIQUID CRYSTAL MATERIALS AND DEVICES CONTAINING SUCH COMPOUNDS

[75] Inventors: David Coates, Hessle; George William Gray, Cottingham, both of England

[73] Assignee: The Secretary of State for Defence in Her Britannic Majesty's Government of the United Kingdom of Great Britain and Northern Ireland, London, England

[21] Appl. No.: 677,820

[22] Filed: Apr. 16, 1976

[30] Foreign Application Priority Data

Apr. 22, 1975  United Kingdom ............ 16643/75

[51] Int. Cl.² ............... G02F 1/13; C09K 3/34; C07C 121/64; C07C 121/60; C07C 121/66

[52] U.S. Cl. ............... 350/160 LC; 252/299; 252/408; 260/465 C; 260/465 D; 260/465 F; 260/465 G; 260/465 K

[58] Field of Search ....... 260/465 G, 465 K, 465 F, 260/465 D, 465 C; 252/299, 408; 350/160 LC

[56] References Cited

U.S. PATENT DOCUMENTS

| | | | |
|---|---|---|---|
| 3,925,238 | 12/1975 | Gavrilovic | 252/299 |
| 3,947,375 | 3/1976 | Gray et al. | 252/299 |
| 3,951,846 | 4/1976 | Gavrilovic | 252/299 |
| 3,952,046 | 4/1976 | Scherrer et al. | 260/463 |
| 3,954,653 | 5/1976 | Yamazaki | 252/299 |
| 3,974,087 | 8/1976 | Gray et al. | 252/299 |

Primary Examiner—Benjamin R. Padgett
Assistant Examiner—T. S. Gron
Attorney, Agent, or Firm—Stevens, Davis, Miller & Mosher

[57] ABSTRACT

A family of new compounds suitable for adding to cyanobiphenyls and other liquid crystal compounds to give mixtures having extended liquid crystal temperature ranges is characterised by the formula

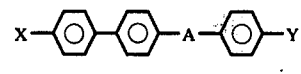

or, a simple substituted derivative thereof, where A is $(CH_2)_n$, $(CH_2)_nO$ $O(CH_2)_n$, $n$ being an integer in the range 1–4, either X is hydrogen or an alkyl, alkoxy or alkanoyloxy group and Y is a cyano group or Y is hydrogen or an alkyl, alkoxy or alkanoyloxy group and X is a cyano group.

The mixtures so produced may be used in known kinds of liquid crystal electro-optic devices.

15 Claims, 2 Drawing Figures

BIPHENYL DERIVATIVE COMPOUNDS AND LIQUID CRYSTAL MATERIALS AND DEVICES CONTAINING SUCH COMPOUNDS

The present invention relates to biphenyl derivative compounds and liquid crystal materials and devices containing such compounds.

United Kingdom Patent Specification No. 1,433,130 describes a family of biphenyl compounds and derivatives useful as liquid crystal materials for a wide range of applications in electro-optic devices such as alphanumeric displays. Copending United Kingdom Patent Application No. 48468/73 (German Offenlegungschrift No. 2,356,085) describes how the liquid crystalline temperature ranges of these biphenyl compounds and derivatives may be extended by forming mixtures from various compounds of the family. One class of mixtures of particular interest is formed from 4-alkyl-or-alkoxy-4'-cyano-biphenyls and 4-alkyl-or-alkoxy-4''-cyano-p-terphenyls.

The present invention provides a family of compounds alternative to the terphenyls suitable for use as additives to 4-alkyl-or-alkoxy-4'-cyano biphenyls to extend the liquid crystalline temperature ranges of the latter.

According to one aspect of the present invention a liquid crystal additive compound has a formula or a simple substituted derivative thereof as defined below, the group A being $(CH_2)_n$ or $(CH_2)_nO$ or $O(CH_2)_n$, $n$ being an integer in the range $1 \leq n \leq 4$, and of the groups X and Y one is a cyano group and the other is hydrogen or an alkyl, alkoxy or alkanoyloxy group.

By a 'simple substituted derivative' is meant a compound having the formula modified by a Cl or $CH_3$ group present as a substituent in any of the benzene rings or by a $>CH_2$, $>C=O$ or $-HC=CH-$ group bridging two ortho positions adjacent to the interannular bond of the biphenyl ring system.

The alkyl, alkoxy or alkanoyloxy group preferably has from one to ten carbon atoms and may be either normal or branched: the branched version may include an optically active center.

Preferably the para-substituent A has two or four carbon atoms if A contains no oxygen atom or one or three carbon atoms if A contains an oxygen atom.

According to another aspect of the invention a liquid crystal material includes a mixture of at least one compound having the formula where R is an alkyl, alkoxy or alkanoyloxy group, together with an additive compound as defined above or a mixture of at least two different compounds having the said formula According to a further aspect of the invention a liquid crystal device inlcudes a layer of the liquid crystal material defined in the previous aspect and means for applying across the layer a bias field capable of altering an optical property of the layer. The bias field may be electric or magnetic. The optical property may for example be refractive index, transmittance or optical activity.

The following Examples describe compounds embodying the invention and the methods of making them.

EXAMPLE 1

Preparation of 1,2 - [4' - (4'' - alkylbiphenylyl) - 4''' -cyanophenyl] ethanes by the following route:

where R is an alkyl group, for example an n-alkyl group.

Step A1: The production of 4-acylbiphenyls (by Friedel-Crafts Acylation)

One example of a way of carrying out this step is as follows:

To commercially available biphenyl (0.08 mole) and anhydrous aluminium trichloride (0.1 mole) dissolved in dry nitrobenzene (90 ml), the appropriate acyl chloride (RCOCl) (0.1 mole) is added in drops, the temperature being maintained at about - 7° C during the addition. The mixture is then stirred for about 18 hrs, with cooling in an ice bath. It is then poured onto a mixture of ice, water and concentrated hydrochloric acid and stirred for 0.5 hr, and the nitrobenzene layer is separated. The nitrobenzene is removed by steam distillation and the residue is crystallised from a small volume of ethanol to constant melting point.

Step B1: The production of 4-alkylbiphenyls (by Huang Minlon Reduction)

One example of a way of carrying out this step is as follows:

To the appropriate ketone (0.037 mole) dissolved in a mixture of dry diethylene glycol (60ml) by warming, a solution of (98%) hydrazine hydrate (0.08 mole) in dry diethylene glycol (20ml) is added. Potassium hydroxide (0.09 mole) is added to the warm solution and water (2ml) is added. The mixture is then heated at 130 –140° C for 2 hrs, and then at 180 –190° C for 4 hrs., whilst a few mls of volatile material are distilled off. On cooling, the reaction mixture is shaken with water and chloroform. The chloroform layer is dried over anhydrous sodium sulphate, then evaporated to complete dryness and the resultant oil or low melting solid is distilled or crystallised from ethanol to constant melting point.

Step C1: The production of 4-(4'-alkylbiphenylyl) 4''-bromophenylmethyl ketones (by Friedel-Crafts Acylation)

One example of a way of carrying out this step is as follows:

A mixture of the appropriate 4-alkylbiphenyl (0.08 mole), 4-bromophenylacetyl chloride (0.1 mole — prepared by standard methods from commercially available 4-bromophenylacetic acid) and dry dichloromethane (140ml) is added in drops to a mixture of dry dichloromethane (50ml) and anhydrous aluminium trichloride (0.12 mole) cooled in an ice/salt bath to −7° C. The mixture is stirred at between −7° and 0° C for 2 hrs, and then at room temperature for 1 hour; it is then poured over ice, water and concentrated hydrochloric acid and the resultant mixture is stirred for 0.5 hr. The dichloromethane layer is separated, washed with water, dried, and evaporated to dryness, and the residue is crystallised from a mixture of ethanol and toluene to constant melting point.

Step D1: The production of 1,2-[4'-(4'''-aklylbiphenylyl)-4''''-bromophenyl] ethanes (by Huang-Minlon Reduction).

This step is carried out in a manner analogous to Step B1, but using more diethylene glycol to dissolve the ketone.

Step E1: The production of 1,2-[4'-(4''-alkylbiphenylyl)-4''''-cyanophenyl] ethanes.

One example of a way of carrying out this step is as follows:

The product from step $D_1$ (1g) is dissolved in dry, hot N-methyl-2-pyrrolidone (2ml); cuprous cyanide (0.5g) is added and the mixture is vigorously stirred under reflux for 1.5 hrs. On cooling, the mixture is poured into a solution of water (30 ml), ferric chloride (3g) and concentrated hydrochloric acid (1ml) and stirred for 0.5 hr. at 60° C. After cooling, the mixture is shaken with chloroform; the chloroform layer is washed with water, dried over anhydrous sodium sulphate and evaporated to dryness. The residue is purified by column chromatography on silicic acid using chloroform as eluent, followed by crystallisation from ethanol until constant transition temperatures are obtained.

EXAMPLE 2

Preparation of 1,2- [4'-(4''-alkoxybiphenylyl)-4''''-cyanophenyl] ethanes by the following route:

where R is an alkyl group, for example a n-alkyl group.

Step A2: The production of 4-alkoxybiphenyls

One example of a way of carrying out this step is as follows:

To a mixture of 4-hydroxybiphenyl (0.033 mole) and anhydrous potassium carbonate (0.132 mole) in cyclohexanone (70ml), the appropriate alkyl bromide (0.053 mole) is added and the stirred mixture heated under reflux for 4 hrs. On cooling, the reaction mixture is filtered, and the solvent is removed from the filtrate. The residue is crystallised from ethanol or light petroleum (b.p 40°–60° C) to constant melting point.

Step B2: The production of 4-(4'-alkoxybiphenylyl)-4''-bromophenylmethyl ketones (by Friedel-Crafts Acylation)

This step is carried out in a manner analogous to step C1, but using 0.24 mole of aluminium trichloride.

Step C2: The production of 1,2-[4'-(4'''-alkoxybiphenylyl)-4''''-bromophenyl] ethanes (by Huang-Minlon Reduction)

This step is carried out in a manner analogous to step D1.

Step D2: The production of 1,2-[4'-(4''-alkoxybiphenylyl)-4''-cyanophenyl] ethanes This step is carried out in a manner analogous to step E1.

EXAMPLE 3

Preparation of 1,2- [4'-(4''-alkanoyloxybiphenylyl)-4'''-cyanophenyl] ethanes by the following route:

where R is an alkyl group, for example an n-alkyl group.

The starting material is the product from step C2 in Example 2, with $R = CH_3$.

Step A3: The production of 1,2-[4'-(4''-hydroxybiphenylyl-4'''-bromophenyl] ethanes Demethylation of the methyl ether is carried out by hydrolysis with a mixture of constant boiling hydrobromic acid and acetic acid according to conventional procedures.

Step B3: The production of 1,2-[4'-(4''-hydroxybiphenylyl)-4'''-cyanophenyl)] ethanes This step is carried out in a manner analogous to step E1 in example 1.

Step C3: The production of 1,2-[4'-(4''-alkanoyloxybiphenylyl)-4'''-cyanophenyl)] ethanes This step is carried out by a conventional technique using the appropriate acyl chloride and a mixture of pyridine and benzene.

EXAMPLE 4

The corresponding 1,4-[4'-(4''-alkyl, alkoxy or acyloxy) biphenylyl)-4'''-cyanophenyl butanes are prepared in an analogous manner to examples 1, 2 and 3 respectively, but using ω-(4-bromophenyl) butyryl chloride, which is prepared by standard methods, instead of 4-bromophenylacetyl chloride.

EXAMPLE 5

Preparation of 1,2- [4'-alkylphenyl-4''-(4'''-cyanobiphenylyl)] ethanes by the following route:

where R is an alkyl group, for example an n-alkyl group.

Step A5: The production of 4-phenylacetyl-4'-bromobiphenyl (by Friedel-Crafts Acylation)

This step is carried out in a manner analogous to step A1 (or C1), the acid chloride being prepared from phenylacetic acid by a conventional method using thionyl chloride.

Step B5: The production of 4-(4''-alkanoylphenylacetyl)-4' bromobiphenyls (by Friedel-Crafts Acylation)

This step is carried out in a manner analogous to step A1.

Step C5: The production of 1,2-[4'-alkylphenyl-4''-(4'''-bromobiphenylyl)] ethanes (by Huang Minlon Reduction)

This step is carried out in a manner analogous to step D1, but using double proportions of hydrazine hydrate, water and potassium hydroxide.

Step D5: The production of 1,2-[4'-alkylphenyl-4''-(4'''-cyanobiphenylyl)] ethanes.

This step is carried out in a manner analogous to step E1.

EXAMPLE 6

The corresponding 1,4-[4'-alkylphenyl-4''-(4'''-cyanobiphenylyl)] butanes are prepared in an analogous manner to Example 5 but using ω-phenylbutyryl chloride in the step corresponding to A5.

EXAMPLE 7

Preparation of 1,2-[4'-alkoxyphenyl-4''-(4'''-cyanoliphenylyl)] ethanes by the following route:

where R is an alkyl group, for example an n-alkyl group.

Step A7: The production of 4-alkoxyphenylacetic acids.

One example of a way of carrying out this step is as follows:

This alkylation is carried out by standard techniques, starting with commercially available 4-hydroxyphenylacetic acid which is heated with the alkyl halide and sodium hydroxide.

Step B7: The production of 4-alkoxyphenylmethyl 4''-(4'''-bromobiphenylyl) ketones (by Friedel-Crafts Acylation)

This step is carried out in a manner similar to step C1, but the reaction mixture is heated for 4 hrs under reflux (instead of being cooled in ice for 2 hrs). The acid chloride used in the Friedel-Crafts acylation is prepared from the product of step A7 by a conventional method using thionyl chloride.

Step C7 and Step D7: These steps are achieved by methods analogous to steps D1 and E1, respectively.

EXAMPLE 8

The corresponding 1,4-[4'-alkoxyphenyl-4''-(4'''-cyanobiphenylyl)]butanes are prepared in a similar manner to Example 7 but using ω-(4-hydroxyphenyl) butyric acid in the step corresponding to A7.

EXAMPLE 9

Preparation of 1,2-[4'-alkanoyloxyphenyl-4''-(4'''-cyanobiphenylyl)] ethanes by the following route:

where R is an alkyl group, for example an n-alkyl group.

The starting material for step A9 is the product from step C7 in example 7, with R equal to $CH_3$.

Step A9: The production of 1,2-[4'-(4'''-bromobiphenylyl)-4''''-hydroxyphenyl]-ethanes.

This step is carried out in a manner analogous to step A3.

Step B9: The production of 1,2-[4'-(4''-cyanbiphenylyl)-4''''-hydroxyphenyl]-ethanes.

This step is carried out in a manner analogous to step E1.

Step C9: The production of 1,2-[4'-alkanoyloxyphenyl-4''-(4''''-cyanobiphenylyl)] ethanes.

This step is carried out in a manner analogous to step C3.

EXAMPLE 10

The corresponding 1,4-[4'-alkanoyloxyphenyl-4''-(4''''-cyanobiphenylyl)] butanes are prepared in an analogous manner using ῶ-(4-methoxyphenyl) butyric acid (prepared as in step A7) followed by demethylation and acylation as in steps A3 and C3 respectively.

EXAMPLE 11

Preparation of 4-(4'-alkylbiphenylyl)oxy-4''-cyanophenylmethanes by the following route:

where R is an alkyl group, for example an n-alkyl group.

Step A11: The production of 4-methoxybiphenyl.

Methylation of 4-hydroxybiphenyl is carried out with dimethyl sulphate according to a conventional method.

Step B11: The production of 4-alkanoyloxy-4'-methoxybiphenyls (by Friedel-Crafts Acylation).

This step is carried out in a manner analogous to step B1.

Step C11: The production of 4-alkyl-4'-methoxybiphenyls (by Huang-Minlon Reduction).

This step is carried out in a manner analogous to step B1.

Step D11: The production of 4-alkyl-4'-hydroxybiphenyls.

This step is carried out by a conventional method analogous to step A3.

Step E11: The production of 4-(4'-alkylbiphenylyl)oxy-4''-cyanophenylmethanes.

This step is carried out by a standard alkylation method analogous to step A2. The required 4-α-bromotolunitrile is commercially available.

EXAMPLE 12

The corresponding 1,3-[4'(4''-alkylbiphenylyl) oxy-4'''-cyanophenyl]propanes are prepared in an analogous manner to Example 11 using ῶ-4-cyanophenylpropyl bromide, prepared by conventional methods, in the step corresponding to E11.

EXAMPLE 13

Preparation of 4-(4'-alkoxybiphenylyl)oxy-4''-cyanophenylmethanes by the following route:

Step B13: The production of 4-(4'-alkoxybiphenylyl)oxy-4''-cyanophenylmethanes.

This step is carried out by a method analogous to step E11.

EXAMPLE 14

The corresponding 1,3-[4'-(4''-alkoxybiphenylyl)oxy-4'''-cyanophenyl] propanes are prepared in a similar manner using ῶ-cyanophenylpropyl bromide in the step corresponding to step B13.

EXAMPLE 15

Preparation of 4-(4'-alkanoyloxybiphenylyl)oxy-4''-cyanophenylmethanes by the following route:

where R is an alkyl group, for example an n-alkyl group.

Step A15: The production of 4-alkanoyloxy-4'-hydroxybiphenyls.

Commercially available 4,4'-dihydroxybiphenyl (2mol) and the appropriate acyl chloride (RCOCl, 1mol) are interacted in dry pyridine. The half ester is separated from the diester and unreacted 4,4'-dihydroxybiphenyl by column chromatography, and the product is finally crystallised to constant melting point from ethanol.

where R is an alkyl group, for example an n-alkyl group.

Step A13: The production of 4-alkoxy4'-hydroxybiphenyls.

Commercially available 4,4'-dihydroxybiphenyl (1 mol) and the appropriate alkyl bromide (1 mol) are heated under reflux for 4 hours with sodium hydroxide (1.5 mole) in ethanol. The half ether is separated from the diether and unreacted 4,4'-dihydroxybiphenyl by a combination of washing procedures and column chromatography as described in the literature, and finally the half ether is crystallised from hexane.

Step B15: The production of 4-(4'-alkanoyloxybiphenylyl)oxy-4''-cyanophenylmethanes.

This step is carried out by a standard alkylation method — see step E11.

EXAMPLE 16

The corresponding 1,3[4'-(4''-acyloxybiphenylyl)oxy-4''-cyanophenyl] propanes are prepared in a similar manner using ῶ-(4-cyanophenyl)propyl bromide, prepared by conventional methods, in the step corresponding to step B15.

EXAMPLE 17

Preparation of 4-(4'-alkylbiphenylyl)-4''-cyanophenoxymethanes by the following route:

where R is an alkyl group, for example an n-alkyl group.

Step 17: The production of 4-acetyl-4'-alkylbiphenyls(by Friedel-Crafts Acylation).

The starting material, the 4-alkylbiphenyl, is prepared as in steps A1 and B1 of example 1, and is then acetylated as in step A1.

Step B17: The production of 4-alkybiphenyl-4'-carboxylic acids.

This step is carried out by a standard method based on sodium hypohalite oxidation of the methyl ketone in aqueous sodium hydroxide and dioxan.

Step C17: The production of 4-alkylbiphenyl-4'-carboxylic acid chlorides.

This step is carried out by a standard method using thionyl chloride.

Step D17: The production of 4-(4'-alkylbiphenylyl) methanol.

The reduction of the acid chloride is carried out using standard techniques involving lithium aluminium hydride in ether.

Step E17: The production of 4-(4'-alkylbiphenylyl)methyl bromide.

This step is carried out by standard methods using phosphorus tribromide.

Step F17: The production of 4-(4'alkylbiphenylyl)-4''-cyanophenoxymethanes.

This step is carried out in a manner analogous to step A2 using 4-cyanophenol.

EXAMPLE 18

For corresponding substituted propane compounds, the product from step E17 is converted by standard methods to 3-(4'(4''-alkylbiphenylyl)propyl bromide, which is then used in the subsequent step corresponding to F17 to yield the 1,3-[4'-(4''alkylbiphenylyl)-4''-cyanophenoxy]propanes.

EXAMPLE 19

Preparation of 4-(4'-alkoxybiphenylyl)-4''-cyano-phenoxymethanes by the following route:

The production of 4-acetyl-4'-alkoxybiphenyls is carried out by steps A19 and B19 using methods analogous to steps A2 and A1, respectively. The final products, the 4-(4'-alkoxybiphenylyl)oxy-4''-cyanophenoxymethanes are prepared in a manner analogous to steps C17 to F17 in example 17.

EXAMPLE 20

1,3-[4'-(alkoxybiphenylyl)oxy-4'''-cyanophenoxy]-propanes are prepared using 3-(4-(4''-alkoxybiphenylyl)propyl bromide prepared from the product of Step F19 as in Example 18.

EXAMPLE 21

Preparation of 4-4'-acyloxybiphenylyl)-4''-cyano-phenoxymethanes by the following route:

where R is an alkyl group, for example an n-alkyl group.

Step A21: The production of 4-(4'-hydroxybiphenylyl)methyl bromides.

The starting material 4-(4'-methoxybiphylyl)methanol is prepared as in Example 19. This is then demethylated with constant boiling hydrobromic acid and acetic acid as in step A3; during this process the CH₂OH group is converted into the CH₂Br group.

Step B21: The production of 4-(4'-alkanoyloxybiphenylyl)methyl bromides.

This step is carried out by a conventional acylation technique similar to step C3.

Step C21: The production of 4-(4'-alkanoyloxybiphenylyl)-b 4''-cyanophenoxymethane.

This step is carried out by a method analogous to step A2, but using 4-cyanophenol.

EXAMPLE 22

The 1,3-[4'-(4''-alkanoyloxybiphenylyl)-4''-cyanophenoxy]propanes are prepared from 3-(4-(4''-methoxybiphenylyl)propyl bromide prepared as in Example 20 using a series of standard synthetic methods.

EXAMPLE 23

Preparation of 1,2-[4'-biphenylyl-4'''-cyanophenyl]ethane by the following route:

Step A23: The production of 4-bromobenzyl 4'-biphenylyl ketone (by Friedel-Crafts Acylation).

This step is carried out in a manner analogous to step C1.

Steps B23 and C13: The final production of 1,2-[(4'-biphenylyl)-4''''-cyanophenyl] ethane

Steps B23 and C23 are carried out by methods respectively analogous to steps D1 and E1.

EXAMPLE 24

With the starting material γ-4-bromophenylbutyric acid, prepared by standard techniques from commercially available materials, a method analogous to Example 23 is used to produce 1,4-[4'-biphenylyl 4''-cyanophenyl] butane.

EXAMPLE 25

Preparation of 1,2-[(4'-cyanobiphenylyl)-phenyl]ethane by the following route:

Step A25: The production of 4-(4'-bromobiphenyl) benzyl ketone.

This step is carried out in a manner analogous to step C1, using the acid chloride derived from commercially available phenylacetic acid.

Steps B25 and C25: The production of 1,2-[4'(4''-bromobiphenylyl)-phenyl]ethane.

These steps are carried out by methods analogous to steps D1 and E1.

EXAMPLE 26

1,4-[4'(4''-cyanobiphenylyl)-phenyl]butane is prepared by an analogous method to Example 25 using ω-phenylpropyl bromide in the step corresponding to step A25.

EXAMPLE 27

Preparation of 4-alkylphenoxy-4'-(4''-cyanobiphenylyl)methanes by the following route:

where R is an alkyl group, for example a n-alkyl group. This synthetic route is very similar to that in Example 17, but uses 4-bromobiphenyl instead of a 4-alkylbiphenyl in step A17, and a 4-alkylphenol (either commercially available or prepared by standard methods) instead of 4-cyanophenol (step F17). Step F27 is carried out in a manner similar to step E1.

EXAMPLE 28

The 1,3-[4'-alkylphenoxy-4''(4'''-cyanobiphenylyl)] propanes are prepared by an analogous method to Example 27 using ω-4-(4'-bromobiphenylyl)propyl bromide, prepared by standard methods from the product of the step corresponding to D27 used in the step corresponding to step E27.

EXAMPLE 29

4-alkoxyphenoxy-4'-(4''cyanobiphenylyl)methanes and 1,3-[(4'-alkoxyphenoxy-4''(4'''-cyanobiphenylyl)] propanes are prepared by a similar synthetic route to that in Example 27 for the alkyl analogues, but a 4-alkoxyphenol is used instead of a 4-alkylphenol in the step corresponding to E27. 4-alkoxyphenols are prepared in a manner analogous to that in step A13.

EXAMPLE 30

Preparation of 4-alkanoyloxyphenoxy-4'-(4'-cyanobiphenylyl)methanes by the following route:

wherein R is an alkyl group, for example a n-alkyl group.

Step A30: The production of 4-alkanoyloxyphenoxy-4'-(4''-bromobiphenylyl) methanes This step is carried out by forming the ether from 4-(4'-bromobiphenylyl) methanol (prepared as in Example 27) and a 4-alkanoyloxyphenol (prepared in an analogous manner to step A15) by using dicyclohexylcarbodi-imide and ether as solvent.

Step B30: The production of 4-alkanoyloxyphenoxy-4'-(4''-cyanobiphenylyl)methanes

This step is carried out in a manner analogous to step E1.

EXAMPLE 31

The 1,3-[4'-alkanoyloxyphenoxy-4''-(4'''-cyanobiphenylyl]propanes are prepared by a similar method using ω-4-(4'-bromobiphenylyl) propanol, prepared by standard methods from 4-(4''-bromobiphenylyl) methanol, in the Step corresponding to A30.

EXAMPLE 32

Preparation of 4-alkylphenyl-4'-(4''-cyanobiphenylyl)oxymethanes by the following route:

where R is an alkyl group, for example a n-alkyl group.

Steps A32 and B32: These are carried out by using standard methods

Step C32: The production of 4-alkylphenyl-4'-(4''-bromobiphenylyl)oxymethanes One example of a way of carrying out this step is as follows:

4-Bromo-4'-benzenesulphonyloxybiphenyl (0.30 mole) (the product of step B32) and the appropriate 4-alkylbenzylbromide (0.33 mole) (commercially available or prepared by standard synthetic routes) are heated under reflux for 4 hrs in dioxan (120 ml) and water (60 ml) containing sodium hydroxide (0.07 mole). The warm reaction mixture is poured into a large volume of water and filtered at the pump. The solid is crystallised from ethanol to constant melting point.

Step D32: The production of 4-alkylphenyl-4'-(4''-cyanobiphenylyl)oxymethanes:

This step is carried out in a manner analogous to step E1

EXAMPLE 33

The 1,3-[4'-alkylphenyl-4''-(4'''-cyanobiphenylyl)oxy] propanes are prepared in a similar manner using ω-(4-alkylphenyl)propyl bromides in the Step corresponding to C32.

EXAMPLE 34

Preparation of 4-alkoxyphenyl-4''-(4'''-cyanobiphenylyl)oxymethanes by the following route:

where R is an alkyl group, for example a n-alkyl group.

Step A34: The production of 4-alkoxybenzaldehydes.

This step is carried out using a standard synthetic method similar to step A2

Step B34: The production of 4-alkoxybenzyl alcohol.

This step is carried using standard synthetic methods involving the use of LiAlH₄ in ether Step C 34: The production of 4alkoxybenzyl bromides This step is carried out using standard synthetic methods using constant boiling hydrobromic acid under mild conditions Step D34: The production of 4-alkoxyphenyl 4'-(4''-bromobiphenylyl)oxymethanes This step is carried out in a manner analogous to step C32.

Step E34: The production of 4-alkoxyphenyl 4'(4''-cyanobiphenylyl)oxymethanes

This step is carried out in a manner analogous to step E1.

EXAMPLE 35

1,3-[4'-alkoxyphenyl-4''-(4'''-cyanobiphenylyl)oxy]propanes are prepared by an analogous method to Example 34 using ω-(4-alkoxyphenyl)propyl bromide, prepared from the product of the step corresponding to C34.

EXAMPLE 36

The substituted propanes in Examples 33 and 35 are prepared by substituting the corresponding ω-4-alkyl-or-alkoxy-phenylpropyl bromides for the 4-alkyl-or-alkoxybenzyl bromides in steps C32 and C34. The phenylpropyl bromides may be prepared by the following route:

Step A36: The production of ω-4-alkyl-or-alkoxy-phenylpropanes

This step is carried out by standard synthetic methods involving the production of the Grignard reagent with Mg in ether, followed by reaction with ethylene oxide.

Step B36: The production of ω-(4-alkyl-or-alkoxy-phenyl)propyl bromides

This step is carried out by standard synthetic methods involving the use of phosphorus tribromide.

Substituted, bridged or optically active compounds embodying the invention may be produced by methods similar to those described above using respectively substituted, bridged or optically active starting materials.

The following tables give examples of the liquid crystalline temperature ranges of compounds and mixtures embodying the invention. In the tables R represents an n-alkyl group having the stated composition, C-N represents solid crystal to nematic liquid crystal transition temperature (°C), C-S represents crystal to smectic liquid crystal transition temperature (°C), S-N represents smectic to nematic liquid crystal temperature (°C) and N-I represents nematic to isotropic liquid transition temperature (°C)

TABLE 1

Compounds having the formula

| R | C-S | S-N | N-I |
|---|---|---|---|
| n-C$_3$H$_7$ | 114 | 93.9 | 173.6 |
| n-C$_4$H$_9$ | 99.5 | 98.8 | 175.4 |
| n-C$_5$H$_{11}$ | 90.5 | 93.5 | 164.7 |
| n-C$_6$H$_{13}$ | 87.2 | 91.3 | 163.2 |
| n-C$_7$H$_{15}$ | 83 | 85.1 | 157.4 |
| n-C$_8$H$_{17}$ | 91 | <80 | 155.9 |

TABLE 2

Compounds having the formula:

| R | C-N | N-I |
|---|---|---|
| C$_2$H$_5$ | 136 | 183.4 |
| n-C$_3$H$_7$ | 127 | 166.4 |
| n-C$_4$H$_9$ | 105 | 166.0 |
| n-C$_5$H$_{11}$ | 87.6 | 155.5 |
| n-C$_6$H$_{13}$ | 74.5 | 155.0 |

TABLE 3

Compounds having the formula

| R | C-S | S-N | N-I |
|---|---|---|---|
| n-C$_7$H$_{15}$ | 61.3 | 125.8 | 147.8 |
| n-C$_8$H$_{17}$ | 72.5 | 144.3 | 148 |

TABLE 4

Compounds having the formula

| R | C-N | N-I |
|---|---|---|
| n-C$_5$H$_{11}$ | 103 | 143.3 |
| n-C$_7$H$_{15}$ | 100 | 136.2 |

TABLE 5

| C-N | N-I |
|---|---|
| 122 | 93.6 |

TABLE 6

| C-N | N-I |
|---|---|
| 145 | 162 |

TABLE 7

The following mixture:

| Mixture Constituent | MOL % | C-N | N-I |
|---|---|---|---|
|  | 63% | 49 | 154 |
|  | 37% | | |

TABLE 8

The following mixture:

| Mixture Constituent | MOL % | C-N | N-I |
|---|---|---|---|
|  | 74.5 | 53.5 | 150 |
|  | 25.5 | | |

TABLE 9

The following mixture:

| Mixture Constituent | MOL % | C-N | N-I |
|---|---|---|---|
|  | 13.6 | 14 | 55 |
| | 86.4 | | |

TABLE 10

| Mixture Constituent | MOL % | C-N | N-I |
|---|---|---|---|
| n-C₇H₁₅O—⟨○⟩—CH₂CH₂—⟨○⟩—⟨○⟩—CN | 14.8 | 14 | 59 |
| n-C₅H₁₁—⟨○⟩—⟨○⟩—CN | 85.2 | | |

TABLE 11

| Mixture Constituent | MOL % | C-N | N-I |
|---|---|---|---|
| n-C₇H₁₅O—⟨○⟩—CH₂CH₂—⟨○⟩—⟨○⟩—CN | 7.5 | 3.5 | 49.4 |
| n-C₅H₁₁—⟨○⟩—⟨○⟩—CN | 59.7 | | |
| n-C₇H₁₅—⟨○⟩—⟨○⟩—CN | 32.8 | | |

TABLE 12

| Mixture Constituent | MOL % | C-N | N-I |
|---|---|---|---|
| n-C₇H₁₅O—⟨○⟩—CH₂CH₂—⟨○⟩—⟨○⟩—CN | 6.8 | 1 | 52.6 |
| n-C₅H₁₁—⟨○⟩—⟨○⟩—CN | 55.2 | | |
| n-C₇H₁₅—⟨○⟩—⟨○⟩—CN | 28.9 | | |
| n-C₅H₁₁—⟨○⟩—⟨○⟩—⟨○⟩—CN | 9.1 | | |

TABLE 13

| Mixture Constituent | MOL % | C-N | N-I |
|---|---|---|---|
| n-C₇H₁₅O—⟨○⟩—CH₂CH₂—⟨○⟩—⟨○⟩—CN | 0.1 | 51.8 | 143 |
| n-C₅H₁₁—⟨○⟩—⟨○⟩—⟨○⟩—CN | 29.9 | | |

TABLE 14

| Mixture Constituent | MOL % | C-N | N-I |
|---|---|---|---|
| n-C₅H₁₁O—⟨○⟩—CH₂CH₂—⟨○⟩—⟨○⟩—CN | 12.4 | 36.7 | 153.2 |
| n-C₆H₁₂O—⟨○⟩—CH₂CH₂—⟨○⟩—⟨○⟩—CN | 24.0 | | |
| n-C₇H₁₅O—⟨○⟩—CH₂CH₂—⟨○⟩—⟨○⟩—CN | 38.0 | | |
| n-C₇H₁₅O—⟨○⟩—⟨○⟩—CH₂CH₂—⟨○⟩—CN | 25.6 | | |

TABLE 15

| Mixture Constituent | MOL % | C-N | N-I |
|---|---|---|---|
| n-C$_7$H$_{15}$O—⟨O⟩—CH$_2$CH$_2$—⟨O⟩—⟨O⟩—CN | 6.5 | | |
| n-C$_6$H$_{13}$O—⟨O⟩—CH$_2$CH$_2$—⟨O⟩—⟨O⟩—CN | 4.2 | | |
| n-C$_6$H$_{13}$O—⟨O⟩—CH$_2$CH$_2$—⟨O⟩—⟨O⟩—CN | 4.2 | 0.5 | 54.2 |
| n-C$_5$H$_{11}$—⟨O⟩—⟨O⟩—CN | 55.8 | | |
| n-C$_9$H$_{15}$—⟨O⟩—⟨O⟩—CN | 29.3 | | |

The compounds per se (Tables 1 to 6) have smectic and nematic liquid crystal phases at temperatures ranges considerably higher than room temperature. Tables 7 to 13 illustrate that the temperature ranges of the liquid crystal phases may be considerably reduced by forming mixtures, which are preferably eutectics.

All of the mixtures listed in Tables 7 to 13 are nematogenic (exhibit only nematic liquid crystal phases). Cholesterogenic mixtures may alternatively be formed in one of the following two ways:

i. by producing a compound embodying the invention having an optically active centre:

eg CH$_3$ . CH$_2$ . C*H . (CH$_3$) CH$_2$ O—⟨O⟩—⟨O⟩—

—CH$_2$ . CH$_2$ . —⟨O⟩—CN;

where the asterisk * denotes the optically active centre, and mixing it with one or more known nematogenic compounds, eg n-C$_5$H$_{11}$ . —⟨O⟩—⟨O⟩—CN and n-C$_6$H$_{13}$ , O—⟨O⟩—⟨O⟩—CN ; or ii. by producing a nematogenic compound or mixture embodying the invention, eg the mixture of Table 12, and mixing with it a known optically active cyanobiphenyl, eg CH$_3$ . CH$_2$ . C*H . (CH$_3$) . CH$_2$O—⟨O⟩—⟨O⟩—CN Mixtures embodying the invention may be employed in any known liquid crystal device, the properties of the mixture (eg whether chloesteric or nematic and whether of positive or negative dielectric anisotropy) being selected to suit the particular device.

Examples of some known devices in which the mixtures may be used are: parallel rubbed devices, twisted nematic devices, Freedericksz effect devices, 'memory' effect devices, cholesteric-to-nematic phase change devices and 'guest-host' devices incorporating a dye.

An example of the preparation and construction of a device which is both a cholesteric-to-nematic phase-change and a guest-host device will now be described with reference to the accompanying drawings, in which.

A suitable cholesteric/dye mixture is produced by adding the constituent compounds of the mixture of Table 12 above together with about 1 to 10% by weight of

CH$_3$ . CH$_2$ . C*H (CH$_3$) . CH$_2$ . O—⟨O⟩—⟨O⟩—CN in a small beaker. A small amount (about 1 or 2% by weight) of a suitable dye, eg β-carotene or Sudan Black, is added to the liquid crystal mixture. The beaker and its contents are heated above the temperature at which the liquid crystal mixture is an isotropic liquid, typically 70° C, and are maintained at this temperature for several minutes. The contents are throughly stirred whilst the temperature is being raised and during the period when the temperature is maintained.

After this period the constituent compounds in the beaker will have dissolved into one another. The beaker and its contents are then allowed to cool. The resultant solution is then introduced into a liquid crystal cell in a known way, eg by capillary action.

Figure 1:
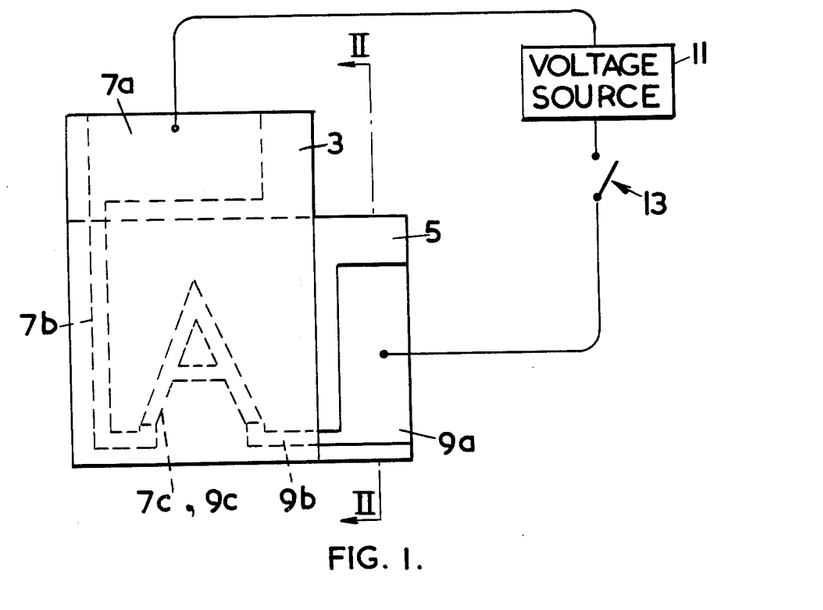
FIG. 1 is a front view of the device.
Figure 2:
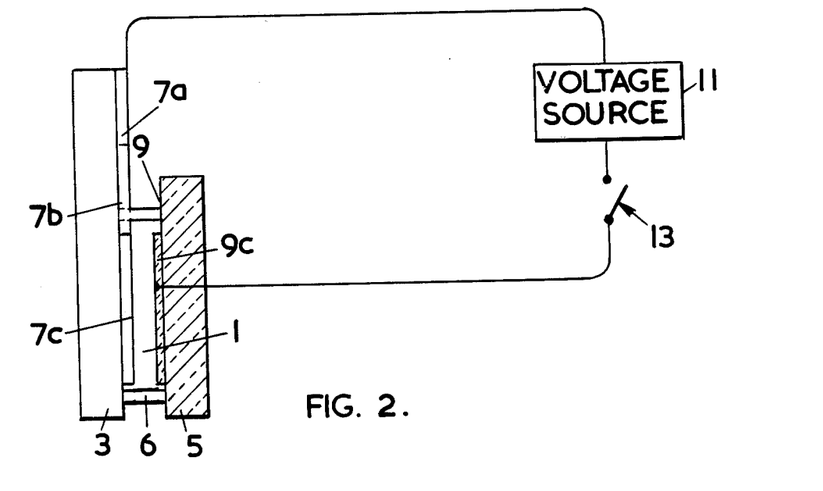
FIG. 2 is a cross-sectional view, partly cut away for clarity, of the device on the line II—II of FIG. 1.

FIGS. 1 and 2 show the cell construction. The cell comprises a layer 1 of the solution of dyed liquid crystal material sandwiched between two parallel rectangular glass slides 3 and 5 having their respective longer edges perpendicular to one another and held apart by a ring-shaped spacer 6 (cut away for clarity in FIG. 2) defining the laterial extremities of the layer 1. The slides 3 and 5 both have on their respective inner surfaces electrodes 7 and 9. The electrode 7 is in the form of a patch 7a on an area of the slide 3 which does not face the slide 5, a strip 7b leading from the patch 7a and a portion 7c attached to the strip 7b and in the form of a letter A. The electrode 9 is in the form of a patch 9a on an area of the slide 5 which does not face the slide 3, a strip 9b leading from the patch 9a and a portion 9c attached to the strip 9b and which is in the form of the letter A. The portion 7c and the portion 9c are arranged to be identical and to face one another.

A voltage source 11 and a switch 13 in series with it are connected between the patch 7a and the patch 9a. The source 11 provides a voltage, which may be either direct or alternating with a low frequency, sufficient to cause re-orientation of liquid crystal and dye molecules in the layer 1 to lie generally in the plane of the slides 3 and 5. A voltage of 10–20 volts will typically be required.

When the switch 13 is open the applied voltage is zero and the liquid crystal and dye molecules are arranged in an array of random helices owing to the chloresteric nature of the liquid crystal material. The layer 1 thus appears strongly coloured with the colour of the dye, eg orange for β-carotene and blue for Sudan Black, since white light incident on the layer 1 has a colour component absorbed by many of the dye molecules particularly those which are perpendicular or oblique to the propagation direction of the light.

When the switch 13 is closed the electric field produced by the voltage source 11 causes the chloresteric to nematic phase change effect to occur. The crystal molecules in the region between the portions 7c and 9c are re-orientated to lie perpendicular to the slides 3 and 5, ie parallel to the electric field, and the dye molecules in this region are re-orientated with the liquid crystal molecules. The layer 1 then appears clear or only weakly coloured between the portions 7c and 9c since the dye molecules do not significantly absorb light propagating along the direction of the electric field, ie along the long axis of the dye molecules. The remainder of the cell appears strongly coloured. If the electric field is removed the dye and liquid crystal molecules all return to their original helical arrangement.

Therefore the letter A may be displayed or not displayed by opening and closing the switch 13.

Preferably, the cell includes a reflector such as a white diffuse reflector, eg white card, a mirror, or a cardboard or plastic screen sprayed with aluminium paint, located behind the slide 5. If the device is then observed from in front of the slide 5 the reflector provides a more uniform background to the letter A.

Other letters, symbols or numerals or parts or groups of them may be displayed in a similar way.

We claim:

1. A compound having the formula (1)

and (2) derivatives thereof having one or more rings substituted with Cl or $CH_3$; and (3) derivatives of (1) or (2) having a group bridging two ortho positions adjacent to the interannular bond of the biphenyl ring system selected from the group consisting of $>CH_2$; $>C=O$ and $-HC=CH-$; wherein A is $(CH_2)_n$; $(CH_2)_nO$ or $O(CH_2)_n$; n is an integer of 1 to 4; and one of the groups X and Y is a cyano group and the other is hydrogen, alkyl, alkoxy or alkanoyloxy.

2. A compound as claimed in claim 1 and wherein A is $(CH_2)_2$.

3. A compound as claimed in claim 1 and wherein A is $CH_2O$ or $OCH_2$.

4. A compound as claimed in claim 1 and wherein X is an alkyl or alkoxy group having from one to ten carbon atoms and Y is a cyano group.

5. A compound as claimed in claim 1 and wherein X is a cyano group and Y is hydrogen or an alkyl or alkoxy group having from one to ten carbon atoms.

6. A compound where n-R is a straight chained alkyl group having five or seven carbon atoms.

7. A liquid crystal mixture including at least one compound as claimed in claim 1 and at least one 4'-alkyl or alkoxy-4-cyanobiphenyl.

8. A compound wherein the group R is a straight chain alkyl group having from three to eight carbon atoms.

9. A compound wherein the group R is a straight chain alkyl group having from two to eight carbon atoms.

10. The compound

11. The compound

12. A liquid crystal mixture comprising a compound as claimed in claim 1 together with at least one other compound selected from the group consisting of said claimed compounds, 4'-alkyl-4-cyanobiphenyls, 4'-alkoxy-4-cyanobiphenyls, 4''-alkyl-4-cyanoterphenyls, and 4''-alkoxy-4-cyanoterphenyls.

13. A liquid crystal mixture as claimed in claim 12 and wherein at least one of the components includes an optically active center so that the mixture exhibits a cholesteric nesophase.

14. An electro-optic device having a layer of liquid crystal material and means for applying an electric field across the layer, wherein the improvement comprises said material being a mixture as claimed in claim 12.

15. An electro-optic device having a layer of liquid crystal material and means for applying an electric field across the layer, wherein the improvement comprises said material being a mixture as claimed in claim 13.

* * * * *